United States Patent
Schneider et al.

(10) Patent No.: US 10,197,528 B2
(45) Date of Patent: Feb. 5, 2019

(54) ISFET MEASURING PROBE, MEASUREMENT CIRCUIT FOR THE ISFET MEASURING PROBE, AND METHOD

(71) Applicant: Mettler-Toledo GmbH, Greifensee (CH)

(72) Inventors: Ingo Andreas Schneider, Cham (CH); Petr Horn, Valens (CH)

(73) Assignee: Mettler-Toledo GmbH, Greifensee (CH)

( * ) Notice: Subject to any disclaimer, the term of this patent is extended or adjusted under 35 U.S.C. 154(b) by 194 days.

(21) Appl. No.: 15/431,856

(22) Filed: Feb. 14, 2017

(65) Prior Publication Data

US 2017/0241944 A1    Aug. 24, 2017

(30) Foreign Application Priority Data

Feb. 24, 2016   (EP) ..................... 16157123

(51) Int. Cl.
| | | |
|---|---|---|
| *G01N 27/416* | (2006.01) | |
| *G01N 27/414* | (2006.01) | |
| *G01N 27/30* | (2006.01) | |
| *G01N 31/22* | (2006.01) | |

(52) U.S. Cl.
CPC ....... *G01N 27/4165* (2013.01); *G01N 27/414* (2013.01); *G01N 27/4148* (2013.01); *G01N 27/4167* (2013.01); *G01N 27/302* (2013.01); *G01N 31/221* (2013.01)

(58) Field of Classification Search
CPC ........ G01N 27/00; G01N 27/26; G01N 27/28; G01N 27/30; G01N 27/302; G01N 27/403; G01N 27/414; G01N 27/4148; G01N 27/4163; G01N 27/4165; G01N 27/4166; G01N 27/4167; G01N 27/42; G01N 31/00; G01N 31/02; G01N 31/22; G01N 31/221
USPC ....... 324/425, 438; 205/775, 787.5, 789, 80, 205/81, 82, 334, 335; 204/193, 194, 204/228.1, 228.6, 400, 401, 433; 203/1, 203/3
See application file for complete search history.

(56) References Cited

U.S. PATENT DOCUMENTS

| | | | |
|---|---|---|---|
| 4,444,644 A | 4/1984 | Hiramoto et al. | |
| 4,777,444 A | 10/1988 | Beijk et al. | |
| 4,879,517 A * | 11/1989 | Connery | ............ G01N 27/4148 324/438 |
| 5,583,462 A | 12/1996 | Grasshoff | |
| 2006/0046375 A1* | 3/2006 | Chou | .................... G01N 27/414 438/216 |
| 2007/0000778 A1 | 1/2007 | Hsiung et al. | |

(Continued)

FOREIGN PATENT DOCUMENTS

| | | |
|---|---|---|
| EP | 0280230 A2 | 8/1988 |
| EP | 0419769 A2 | 4/1991 |
| WO | 01/31326 A1 | 5/2001 |

*Primary Examiner* — Hoai-An D. Nguyen
(74) *Attorney, Agent, or Firm* — Standley Law Group LLP (57) ABSTRACT

ISFET measuring probe with a housing in which an ISFET and a reference electrode are arranged in such a way that the gate electrode of the ISFET, which is coated with an ion-sensitive layer, and the reference electrode reach into a measurement space into which a measurement medium can be introduced, with the distinguishing feature that an auxiliary electrode is arranged additionally inside the housing and is held inside the measurement space.

17 Claims, 3 Drawing Sheets

(56) References Cited

U.S. PATENT DOCUMENTS

2010/0116689 A1* 5/2010 Greene ................ D06F 35/003
205/743
2015/0091581 A1* 4/2015 Sohbati .............. G01N 27/4145
324/464

* cited by examiner

ISFET MEASURING PROBE, MEASUREMENT CIRCUIT FOR THE ISFET MEASURING PROBE, AND METHOD

CROSS-REFERENCE TO RELATED APPLICATIONS

This application is entitled to benefit of a right of priority from European Patent Application No. 16157123.7, filed on 24 Feb. 2016. The content of that application is incorporated by reference as if fully recited herein.

TECHNICAL FIELD

The disclosed invention concerns an ISFET (Ion Sensitive Field Effect Transistor) measuring probe, a measurement circuit for the ISFET measuring probe, and a method, by means of which the condition of a diaphragm of a reference electrode of a pH-measuring probe can be determined.

BACKGROUND

In research laboratories and in different areas of industry such as chemicals, food, biotechnology or pharmaceuticals, measurement electrodes or measuring probes are used to determine the pH-value in a measurement medium. The pH-value of a measurement medium is indicative of the condition, taste or quality of the measurement medium. In chemical processes, the pH-value is also used to control the manufacturing processes.

The pH measurement is carried out according to the principle of a potentiometric measurement. In a potentiometric measurement, a measurement electrode (ISFET) and a reference are immersed in the measurement medium. Through the reference electrode, a defined potential is set up relative to the measurement medium. By measuring, the difference between the respective potentials of the reference electrode and the measurement electrode, the pH-value of the measurement solution can be determined.

Reference electrodes include for example a housing containing a reference electrolyte which, by way of an interface, is in contact with a measurement medium. The interface can be for example an open passage, or it can be configured as a porous diaphragm. The interface should on the one hand have a minimal electrical resistance and should on the other hand impede the mixing of the reference- or bridge electrolyte with the measurement medium. Different measures aim to accomplish these objectives.

The diaphragm of the measuring probe which is in direct contact with the medium on which the measurement is performed is a very sensitive part of the measuring probe. A known problem is the so-called bio-fouling, i.e. foreign substances settling and accumulating on the diaphragm surface and interfering with the measurement. The acidity, fat content, volume and pressure of the measurement medium are factors that can have a negative effect on the operation and on the useful life of the diaphragm.

It is an essential quality of reference electrodes that they maintain, as much as possible, a constant reference potential. This requires that the diaphragm has a constant electrical resistance that should be as small as possible. It is therefore advantageous to check the condition of the diaphragm regularly during operation in order to obtain reliable measurements of the ion concentration.

In pH glass electrodes, diagnostic circuits are used for the purpose of monitoring the condition of the diaphragm and providing status messages, so that the user can terminate the measurement and exchange the sensor at the right time.

Glass electrodes have the disadvantage that the existing diagnostic circuits require additional components. They generate heat which compromises the measurement results and makes it necessary to take corrective measures.

Glass electrodes have the further disadvantage that they are very fragile. In the case of a breakage, the glass fragments would become mixed up in the process material and would consequently pose a danger to the consumer. The use of glass electrodes is therefore normally avoided in a number of areas, for example in biopharmaceuticals and in the food- and beverage industry. Due to these problems, the use of glass electrodes is even legally banned in some areas of industry.

Ion-sensitive field effect transistors (ISFET) are better suited than glass electrodes for these applications, because they are mechanically very stable and nearly unbreakable in comparison to glass electrodes. These properties favor the use of ISFET sensors in areas such as for example the food industry and the pharmaceutical industry, where it is particularly important to protect the process material.

The determination of the pH-value of a measurement medium with a measuring probe that includes an ISFET is based on measuring the behavior of the ISFET. The latter is arranged in the measuring probe so that the gate, which is covered with an ion-sensitive layer, can be brought into contact with the measurement medium. The measuring probe further includes a reference electrode which is likewise immersed in the medium and to which a biasing voltage is applied that determines the electrical potential of the measurement medium and thus the operating point of the ISFET. According to Nernst's equation, a surface potential which depends on the ion concentration in the measurement medium establishes itself in the contact area between the measurement medium and the ion-sensitive layer at the gate of the ISFET. This potential adds itself to the biasing voltage that is applied constantly to the reference electrode and thus affects the depletion zone between source and drain.

Under the conventional method of measuring the pH-value of a measurement medium by means of an ISFET the drain current and the drain potential are held constant, and the source potential is measured. As an alternative, the bias voltage at the reference electrode can be varied and the drain current can thereby be held constant. In this case, the regulated bias voltage serves as the measure for the ion concentration that is present.

Measuring probes with an ISFET have a diaphragm which allows the reference electrode to have access to the measurement medium. For the measurement of the ion concentration to deliver valid results, it is necessary to ensure that a change in the condition of the diaphragm due to detrimental influence factors such as acid, grease and pressure does not affect the measurement.

The condition of the diaphragm can be determined by measuring its electrical resistance. In state-of-the-art diagnostic procedures for ISFET measuring probes the measuring probe has to be taken out of the measurement medium in order to examine the condition of the diaphragm.

The object of the invention is to propose an improved ISFET measuring probe, in particular a pH-measuring probe, as well as a measurement circuit and a method whereby the condition of this measuring probe can be determined.

In particular, the invention aims to provide a diagnostic circuit which allows an in-situ diagnosis, i.e. a diagnosis which does not require the measuring probe to be removed from the measurement medium and which examines the condition of the reference electrode during operation. For reliable measurement results, the diagnostic circuit should only have a small number of components and should only consume a minimal amount of electrical current.

SUMMARY

This task is solved with a measurement circuit, a measurement probe utilizing the measurement circuit and an ISFET, and a method for use of the probe.

The ISFET measuring probe according to the invention includes a housing in which an ISFET and a reference electrode are arranged in such a way that the gate electrode of the ISFET, which is covered with an ion-sensitive layer, and the reference electrode reach into a measurement space into which a measurement medium can be introduced. Also arranged inside the housing is an auxiliary electrode which is designed to be in contact with the measurement medium and is kept within the measurement space.

The measurement circuit serves for the operation of an ISFET measuring probe as disclosed and allows the measurement of the ion concentration in a measurement medium as well as the diagnosis of the measuring probe. The latter includes a reference electrode designed for immersion in the measurement medium and an auxiliary electrode likewise immersible in the measurement medium, as well as an ISFET whose coated gate electrode serves to make contact with the measurement medium. The drain terminal of the ISFET is connected to a first potential of a constant first voltage source, the source terminal is connected to a first terminal of a measurement resistor whose second terminal is connected to a second potential of the first voltage source. The measurement circuit further includes an operational amplifier whose non-inverting input is connected to a settable controlling voltage, whose inverting input is connected to the first terminal of the measurement resistor and whose output is connected to the reference electrode.

The inventive concept includes at least one controllable switch which can be selectively set to a measurement position in which the measurement of the measurement medium takes place, or to at least one diagnostic position in which the diagnosis of the measuring probe takes place. In the diagnostic position of the switch, the auxiliary electrode which is additionally immersible in the measurement medium can be connected to a test voltage, and in the measurement position the auxiliary electrode can be separated from the test voltage.

A bias voltage or reference voltage which is applied to the reference electrode defines the potential of the measurement medium. Beyond a certain value of the reference voltage, the ISFET changes to the conductive state, resulting in a current flow between drain and source. In the following, the reference voltage will be selected so that the ISFET can be operated in a linear operating range.

In a first design of the measurement circuit, the reference voltage is preferably regulated by means of an operational amplifier in such a way that the drain-source current flowing through the measurement resistor remains constant. To accomplish this, the non-inverting input of the operational amplifier is connected to an adjustable controlling voltage by means of which a desired bias voltage or reference voltage can be set at the reference electrode. Across the measurement resistor through which the drain-source current is flowing, a regulating voltage is tapped off and applied to the inverting input of the operational amplifier. This configuration of the measurement circuit has the advantage that the reference voltage varies in linear proportion to the pH-value over a wide range and is thus proportional to the ion concentration of the measurement medium.

The auxiliary electrode is for example an ORP (Oxidation-Reduction Potential) electrode. In the present invention, the auxiliary electrode is used in the diagnostic position of the switch in order to impose a current pulse on the reference electrode. Based on the response signal of the reference electrode and/or the response signal of the auxiliary electrode, a signal can be derived which represents a measure for the resistance of the diaphragm that is arranged at the reference electrode.

The current pulse is generated by means of a constant test voltage which may be applied to the auxiliary electrode by way of a load resistor and a switch. Thus a current flowing between the auxiliary electrode and the reference electrode is independent of the properties of the ISFET, which is preferably switched out during the diagnosis. Based on the measurement of the current or the time profile of the current, the resistance or the conductivity of the reference electrode can be determined. As the detrimental influence factors will change the resistance of the diaphragm, the method according to the invention thus makes it possible to determine the condition of the reference electrode.

In comparison to the conventional pH measurement circuit, the circuit for the diagnosis of the reference electrode only requires the addition of an auxiliary electrode, a load resistor, a switch, and a voltage source to provide the test voltage. These components can be advantageously incorporated in the measurement circuit according to the invention so that besides the measurement of the ion concentration of the measurement medium, the condition of the reference electrode can additionally be determined. It is particularly advantageous that the measuring probe of the expanded configuration according to the invention no longer needs to be removed from the measurement medium in order to evaluate the condition of the reference electrode. The diagnosis can take place within a short time span between two measurement periods, so that the operation of the measuring device is practically not curtailed.

The test voltage can be obtained from different voltage sources. To provide the test voltage, an additional voltage source can be included in the design. As an alternative, since the ISFET is not needed during the diagnosis of the reference electrode, a potential of the operating voltage, for example the potential at the drain terminal, can be used as test voltage during the diagnosis. As a further possibility, the constant controlling voltage that is applied to the non-inverting input of the operational amplifier can be used as test voltage. Since the voltage difference between the non-inverting input and the inverting input of the operational amplifier is close to zero, the constant controlling voltage can also be taken from the inverting input of the operational amplifier.

The test voltage can be connected from one of the aforementioned voltage sources to the auxiliary electrode simply by changing the status of a switch, for example a bipolar or multi-polar switch.

Using a single voltage source for several tasks, for example alternatingly for the operation of the ISFET and to supply the test voltage, has the advantage that the measurement circuit can have a simpler and more cost-effective configuration and requires fewer components, which reduces the amount of undesirable heat dissipation. When the voltage source is switched over, the drain- or source connection can be separated from the rest of the circuit. This has the advantage that there is no load on the ISFET during the diagnostic phase.

The method disclosed serves to measure the ion concentration in a measurement medium and to perform the diagnostic test of a measuring probe as disclosed which includes a reference electrode designed for immersion in the measurement medium and an auxiliary electrode likewise immersible in the measurement medium, as well as an ISFET whose coated gate electrode serves to make contact with the measurement medium, wherein the drain terminal of the ISFET is connected to a first potential of a constant first voltage source, the source terminal is connected to a first terminal of a measurement resistor whose second terminal is connected to a second potential of the first voltage source, wherein the measurement circuit further includes an operational amplifier whose non-inverting input is connected to a settable controlling voltage, whose inverting input is connected to the first terminal of the measurement resistor and whose output is connected to the reference electrode. The inventive concept further includes at least one controllable switch which can be flipped between a measurement position where, in a measurement mode, the measurement of the measurement medium takes place, and at least one diagnostic position where, in a diagnostic mode, the diagnostic test of the measuring probe takes place. In the diagnostic mode, the auxiliary electrode is connected by way of a load resistor to a test voltage in order to measure a first time profile of the voltage on the reference electrode and/or a first time profile of the voltage on the auxiliary electrode. In accordance with the invention, the condition of the reference electrode is determined by comparing the first time profile of the voltage on the reference electrode and/or the first time profile of the voltage on the auxiliary electrode and/or the difference of the first time profile of the voltage on the reference electrode and the first time profile of the voltage on the auxiliary electrode against characteristic values or characteristic curves and by evaluating the comparison values obtained thereby.

The claimed method has the following steps: applying a test voltage to the auxiliary electrode; separating the test voltage from the auxiliary electrode and simultaneously measuring the voltage at the auxiliary electrode as a function of time; measuring the reference voltage at the reference electrode as a function of time; subtracting the two voltage profiles and storing the voltage difference as a function of time as the response signal of the reference electrode; evaluating the response signal and determining the condition of the reference electrode based on the response signal of the reference electrode.

The method according to the invention serves to measure the ion concentration in a measurement medium and to perform a diagnostic test on a measuring probe as disclosed which includes a reference electrode designed for immersion in the measurement medium and an auxiliary electrode likewise immersible in the measurement medium, as well as an ISFET whose coated gate electrode serves to make contact with the measurement medium, preferably with a measurement circuit as disclosed wherein the drain terminal of the ISFET is connected to a first potential of a constant first voltage source, the source terminal is connected to a first terminal of a measurement resistor whose second terminal is connected to a second potential of the first voltage source. The measurement circuit further includes an operational amplifier whose non-inverting input is connected to a settable controlling voltage, whose inverting input is connected to the first terminal of the measurement resistor and whose output is connected to the reference electrode. The inventive concept further includes at least one controllable switch which can be selectively set to a measurement position where, in a measurement mode, the measurement of the measurement medium takes place, and to at least one diagnostic position where, in a diagnostic mode, the diagnostic test of the measuring probe takes place.

According to the invention, when the circuit is switched to the diagnostic mode, i.e. during the in situ diagnosis, the auxiliary electrode is connected preferably by way of a load resistor to a test voltage. Next, a first time profile of the voltage at the reference electrode and/or a first time profile of the voltage at the auxiliary electrode is measured. Subsequently, the first time profile of the voltage on the reference electrode and/or the first time profile of the voltage on the auxiliary electrode and/or the difference of the first time profile of the voltage on the reference electrode and the first time profile of the voltage on the auxiliary electrode is compared to characteristic values or characteristic curves in order to establish comparison values. Finally, the comparison values are evaluated and the condition of the reference electrode is determined.

The test criteria are preferably: whether the measured time profiles of the voltages of the reference electrode and/or of the auxiliary electrode or the time profile of the signal representing the difference lie within a zone of tolerance, or whether the time profiles do not exceed predetermined threshold values. As an alternative, the evaluation of the response signal and/or of the measured time profiles of the voltages can be performed as a comparison against reference time profiles. Characteristic curves and characteristic values, such as tolerance zone and threshold values, can be established for example based on the examination of measuring probes that have been in operation over an extended length of time.

In the method for the in-situ diagnosis of the reference electrode, the ISFET source- and/or drain connection is preferably separated from the rest of the measurement circuit while a constant test voltage is applied to the auxiliary electrode.

With preference, the test voltage is applied to the auxiliary electrode by way of a load resistor.

The test voltage can advantageously be tapped off the inverting input of the operational amplifier. As the voltage difference between the inverting and the non-inverting input of the operational amplifier is practically zero, the tapped test voltage equals the controlling voltage that is present at the non-inverting input. As the ISFET source terminal is connected by way of the measurement resistor to a potential of the operating voltage, the test voltage can also advantageously be tapped off this first termination of the measurement resistor.

With preference, a voltage pulse of a first polarity, a first predefined amplitude, and a first predefined duration is applied to the auxiliary electrode.

With preference, a first voltage pulse of a first polarity, a first predefined amplitude, and a first predefined duration, followed by a second voltage pulse of a second polarity which is the opposite of the first polarity, a second predefined amplitude, and a second predefined duration is applied to the auxiliary electrode.

BRIEF DESCRIPTION OF THE DRAWINGS

In the following, the measuring probe according to the invention, the measurement circuit according to the invention and the method according to the invention will be explained in their different embodiments with the help of drawings, wherein FIG. 1 schematically represents a measuring probe M according to the invention with an ISFET T, a reference electrode RE, and an auxiliary electrode AUX, which are connected to a measurement circuit MC according to the invention.

DETAILED DESCRIPTION

Figure 1:
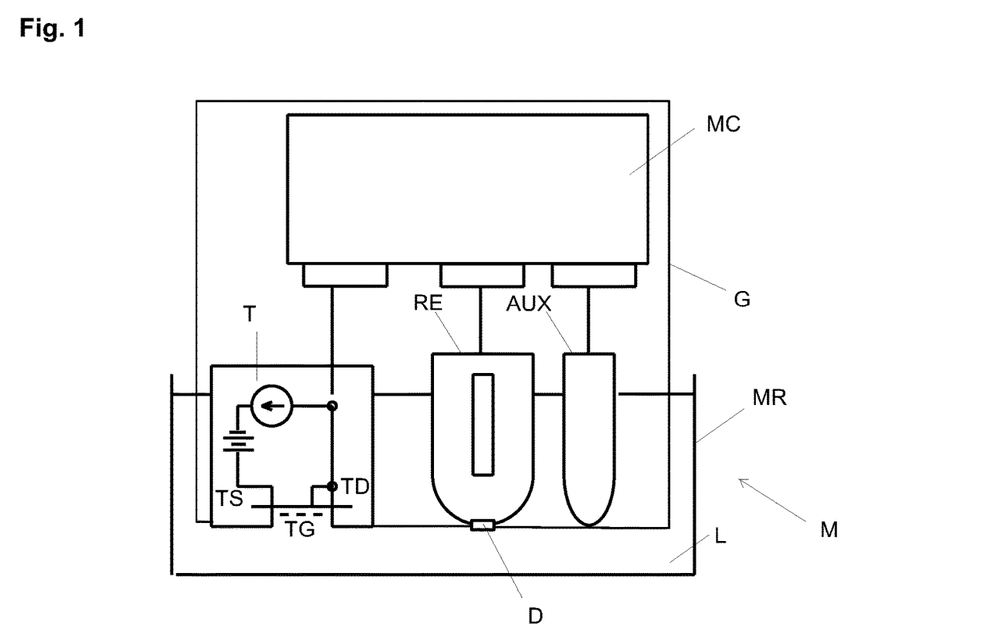

FIG. 1 schematically illustrates a measuring probe M according to the invention with an ISFET T, a reference electrode RE, an auxiliary electrode AUX, and a measurement circuit MC according to the invention which are arranged in a housing G. The measuring probe M is shown in the operating state while performing a measurement. The ISFET T, the reference electrode RE and the auxiliary electrode AUX are connected to a measurement circuit MC and are immersed in a measurement solution L which is contained in a measurement space. The measurement circuit MC generates and processes electrical signals in order to determine the ion concentration of the measurement solution L and the condition of the measuring probe M. The reference electrode RE has a diaphragm D which serves to capture the potential of the measurement solution L and whose condition is monitored in a diagnostic procedure.

Figure 2:
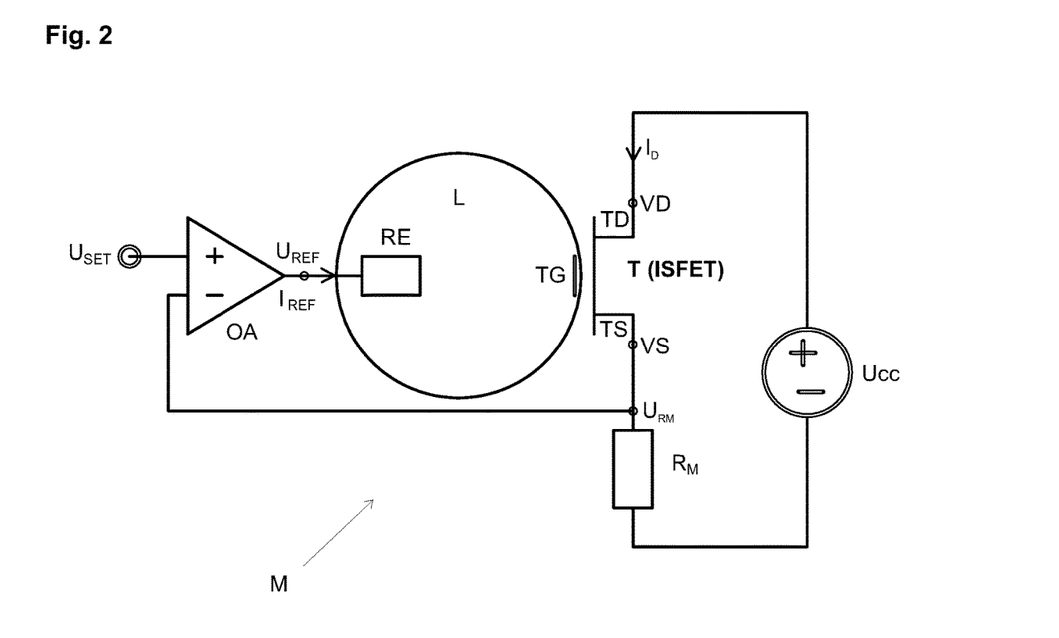
FIG. 2 schematically represents a conventional measurement circuit with an ISFET T for the measurement of the ion concentration in a measurement medium L.

FIG. 2 schematically illustrates a conventional circuit MC for the measurement of the ion concentration in a measurement solution L by means of a measuring probe M which contains an ISFET T and a reference electrode RE. The ISFET drain terminal TD is connected to a first potential of the constant operating voltage $U_{CC}$. The ISFET source terminal TS is connected to a measurement resistor $R_M$ whose second termination is connected to a second potential of the operating voltage $U_{CC}$. In the operating state for taking measurements, a drain-source current $I_D$ is accordingly flowing through the ISFET and continuing through the measurement resistor $R_M$ towards the second potential of the operating voltage $U_{CC}$. During operation in measurement mode, the ISFET gate TG which is coated with an ion-sensitive layer is in direct contact with the measurement medium L in which the measuring probe M is immersed. The ion-sensitive layer consists for example of $Si_3N_4$, $Al_2O_3$ or $Ta_2O_5$.

The potential at the reference electrode RE corresponds to the potential of the measurement medium L. The voltage of the reference electrode RE is in this context considered in relation to the negative supply voltage of the operational amplifier OA. The operating voltage $U_{CC}$ can be derived from the supply voltage of the operational amplifier OA, for example by way of a series resistor, as the drain-source current $I_D$ is kept constant for example by a regulating circuit. The ion concentration of the measurement medium L contacted by the ISFET gate TG affects the depletion zone and has a direct influence on the drain-source current $I_D$ in the ISFET T. The ion concentration can be determined in different ways. In the circuit of FIG. 2 the voltage at the reference electrode RE, i.e. the reference voltage $U_{REF}$, is regulated by means of an operational amplifier OA in such a way that the drain-source current $I_D$ remains constant.

To accomplish this, an adjustable controlling voltage $U_{SET}$ is applied to the non-inverting input of the operational amplifier OA. The inverting input of the operational amplifier OA is connected to a regulating voltage $U_{RM}$ which is tapped off the first connection of the measurement resistor $R_M$. The output of the operational amplifier OA, which is connected to the reference voltage $U_{REF}$, is connected to the reference electrode RE. Accordingly, the reference voltage $U_{REF}$ depends on the one hand on the controlling voltage $U_{SET}$ and on the other hand on the regulating voltage $U_{RM}$ that is taken off the measurement resistor $R_M$.

The controlling voltage USET is preferably set at a level where the potential of the reference voltage RE in the measurement solution L lies about midway in the range of the supply voltage of the operational amplifier OA when the measurement solution has a neutral pH-value (pH=7). This ensures an optimal range of variation for alkaline and acidic solutions. The controlling voltage $U_{SET}$ is subsequently held constant and can be derived by means of a voltage divider from the supply voltage of the operational amplifier OA or from the operating voltage $U_{CC}$. The schematic representation of FIG. 2 thus reduces the circuit to its essential functionality.

With increasing ion concentration in the measurement medium L, the drain-source current $I_D$ in the ISFET rises up and so does, accordingly, the voltage across the measurement resistor $R_M$, which is connected as regulating voltage $U_{RM}$ to the inverting input of the operational amplifier OA. The operational amplifier OA accordingly reduces the reference voltage $U_{REF}$.

The reference voltage $U_{REF}$ is therefore regulated so that the voltage differential across the measurement resistor $R_M$, i.e. the regulating voltage $U_{RM}$ and thus also the drain-source current $I_D$, are held constant. The reference voltage $U_{REF}$ changes in linear proportion to the pH-value and therefore represents a measure for the ion concentration in the measurement medium L. Normally, the reference current $I_{REF}$ flowing into the measurement medium L is at zero, as long as the gate TG is insulated from the ISFET and has a very high resistance.

Figure 3:
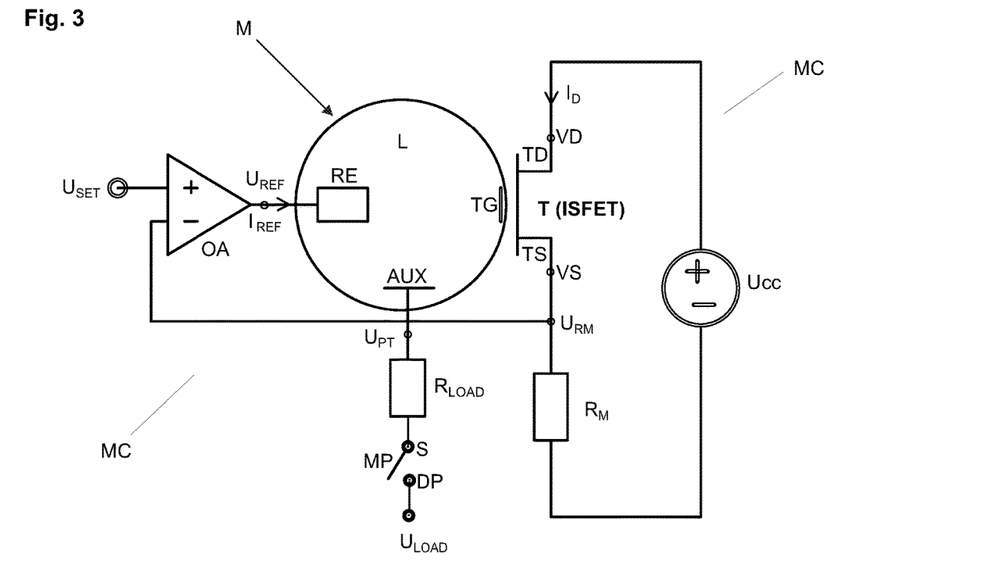
FIG. 3 schematically represents an ISFET measuring probe M according to the invention, in which an auxiliary electrode AUX is additionally incorporated, as well as a measurement circuit with an operational amplifier OA for the measurement of the ion concentration in a measurement medium and for the determination of the condition of the measuring probe M by mans of the incorporated auxiliary electrode AUX.

FIG. 3 schematically represents an ISFET measuring probe M according to the invention, in which an auxiliary electrode AUX is incorporated, as well as a measurement circuit according to the invention for the measurement of the ion concentration in a measurement medium L and for the determination of the condition of the measuring probe M by mans of the incorporated auxiliary electrode AUX. The measurement circuit can be operated in a measurement mode where the ion concentration of the measurement medium L is measured, and in a diagnostic mode where the condition of the measuring probe M is determined.

The circuit arrangement of FIG. 3 is analogous to the circuit of FIG. 2, except that the circuit of FIG. 3 additionally includes an auxiliary electrode AUX which, by way of a load resistor $R_{LOAD}$ in series with a switch S that is set to the position DP can be connected in the diagnostic mode to a voltage source $U_{LOAD}$ which is provided by an external voltage generator. In the position DP of the switch S, the test voltage $U_{PT}$ is accordingly connected to the auxiliary electrode AUX. In the measurement mode, the switch S is opened, i.e. set to the position MP, and the auxiliary electrode AUX is accordingly not under load.

In the diagnostic mode, the switch S is temporarily closed, so that during the respective time interval the voltage source $U_{LOAD}$ is connected to the auxiliary electrode AUX by way of the load resistor $R_{LOAD}$. Thus, a diagnostic current pulse $I_{REF}$ is imposed on the auxiliary electrode AUX. As a result, a current flows in the measurement medium L between the auxiliary electrode AUX and the reference electrode RE. The time profile of the voltage at the reference electrode RE and/or the time profile of the voltage at the auxiliary electrode AUX can subsequently be registered and evaluated. With preference, the difference between the two voltage profiles is determined and evaluated. By comparing the individual voltages or their difference to characteristic values or characteristic curves, for example reference graphs, threshold values or limits, the condition of the measuring probe M can be determined. The examination includes for example whether the measured voltage profiles lie within a tolerance zone, or whether resulting deviations from the reference profiles exceed a threshold value.

Figure 4:
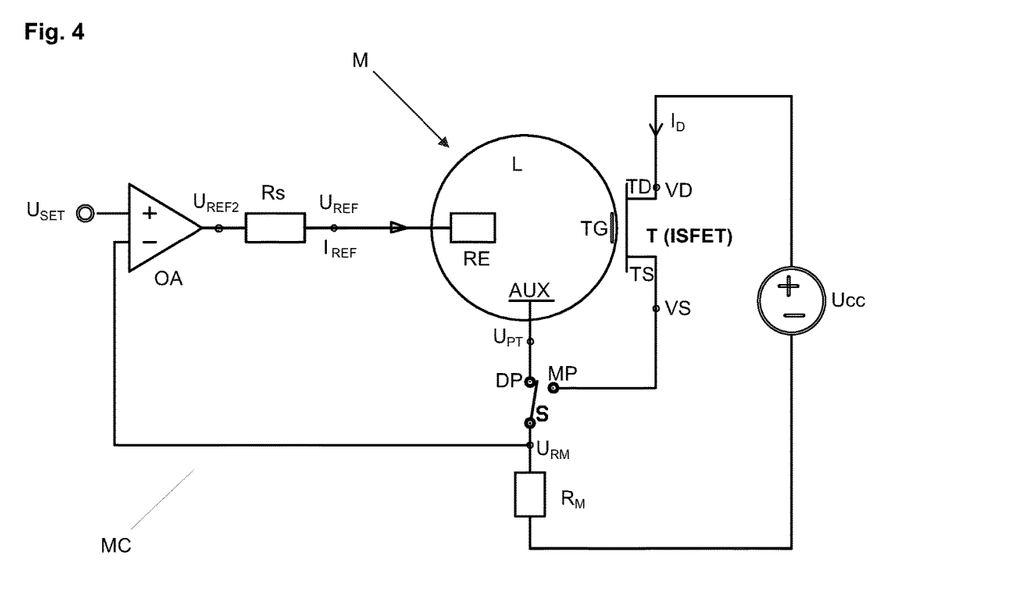
FIG. 4 shows the measuring probe M and the measurement circuit of FIG. 3, wherein the operational amplifier OA selectively functions to regulate the ISFET source-drain current or as a galvanostat to generate a diagnostic current $I_{REF}$ flowing through the auxiliary electrode, which causes a measurable voltage jump due to the internal resistance RS of the reference electrode RE.

FIG. 4 shows an embodiment of the measurement circuit MC in which no separate voltage source $U_{LOAD}$ is used. Instead, a multi-polar switch or selector switch S which is connected to the first termination of the measurement resistor $R_M$ and the inverting input of the operational amplifier OA can be set either for the measurement position MP which connects to the source terminal TS of the ISFET, or for the diagnostic position DP which connects to the auxiliary electrode AUX. Accordingly, in the diagnostic position DP, the auxiliary electrode AUX is connected to the voltage that is present at the inverting input of the operational amplifier OA, which corresponds to the controlling voltage $U_{SET}$ that is present at the non-inverting input of the operational amplifier OA.

Accordingly, the voltage at the connection between the measurement resistor RM and the inverting input of the operational amplifier OA serves as a second constant voltage source. By changing the position of the switch S, the ISFET source terminal TS is at the same time separated from the rest of the circuit, so that the ISFET T is not under load during the diagnostic test.

In the measurement position MP, the operating point of the ISFET, in particular the drain-source current and the drain-source voltage, is defined by the controlling voltage $U_{SET}$ and the measurement resistor $R_M$.

In the diagnostic position DP, the diagnostic current $I_{REF}$ which is flowing in the auxiliary electrode AUX is defined by the controlling voltage $U_{SET}$ and the value of the measurement resistor $R_M$ which are preferably controllable. The diagnostic current $I_{REF}$ causes a measureable, time-dependent voltage jump ($U_{REF2}$-$U_{REF}$) across the internal resistance $R_S$ of the reference electrode RE, whereby the internal resistance $R_S$ of the reference electrode RE can be determined.

With preference, the controlling voltage $U_{SET}$ and the value of the measurement resistor $R_M$ are programmed so that in the measurement position MP and in the diagnostic position DP the desired operating point is set for the ISFET and the desired diagnostic current $I_{REF}$ is imposed on the auxiliary electrode AUX.

Figure 5:
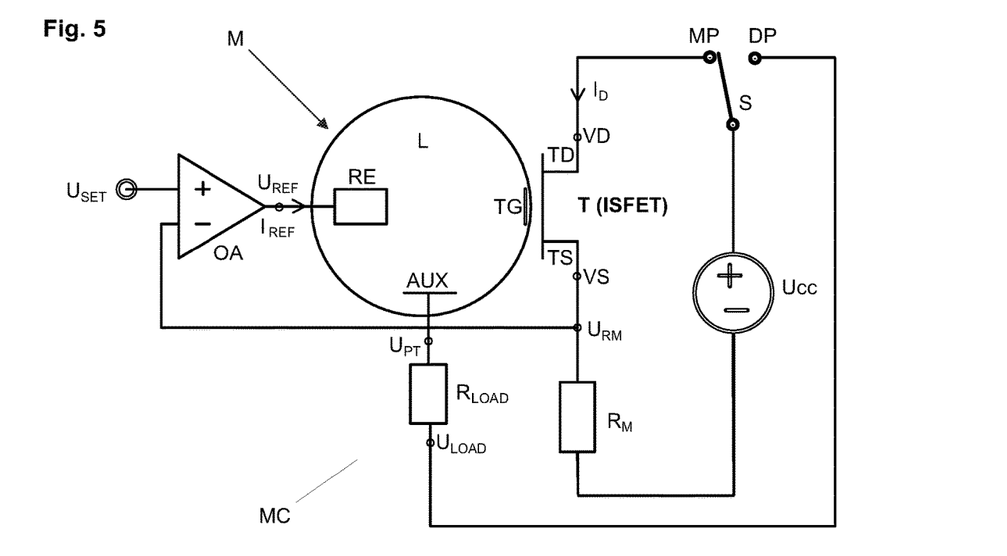
FIG. 5 shows the measuring probe M and the measurement circuit of FIG. 3, wherein the operating voltage can be switched between the ISFET drain terminal TD and the auxiliary electrode AUX.

FIG. 5 shows a further preferred embodiment of the measurement circuit MC wherein no additional voltage source is used, but wherein the operating voltage $U_{CC}$ is used instead as a second constant voltage source. The multi-polar switch or selector switch S is connected on the one hand to a potential of the operating voltage $U_{CC}$ and can on the other hand be set either to the measurement position MP which connects to the drain terminal TD of the ISFET or to the diagnostic position DP which connects by way of the load resistor $R_{LOAD}$ to the auxiliary electrode AUX. Accordingly, in the measurement position MP of the switch S, the auxiliary electrode AUX is separated from the rest of the circuit, and in the diagnostic position DP of the switch S the flow of current through the ISFET T is interrupted and the latter is not under load. Based on the jump in the time profile of the reference voltage $U_{REF}$ as a result of the imposed diagnostic current $I_{REF}$ which flows through the auxiliary electrode AUX and is regulated, the value of the internal resistance of the reference electrode RE can be determined.

Figure 6:
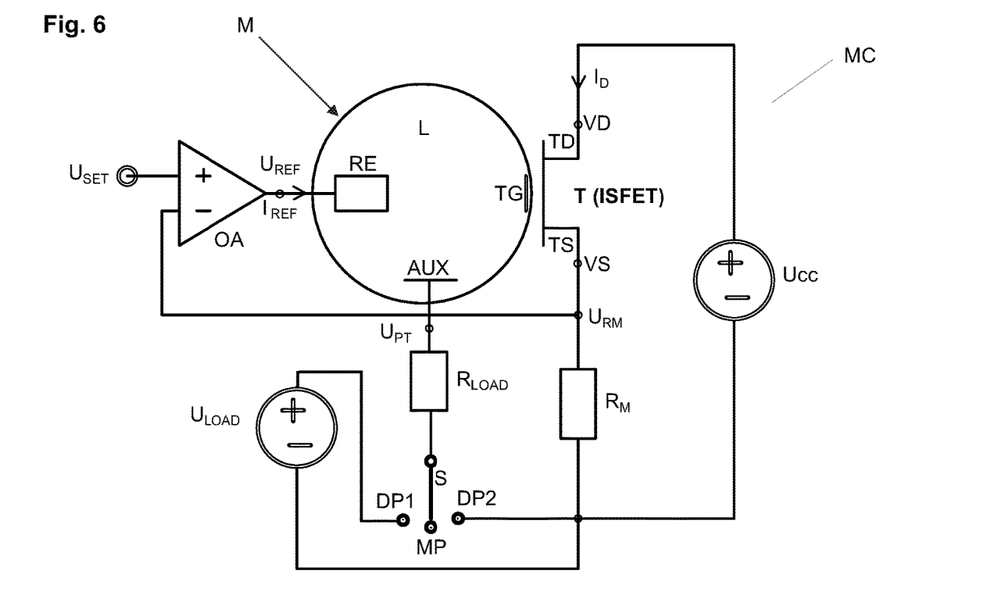
FIG. 6 shows the measuring probe M and the measurement circuit of FIG. 3, wherein the auxiliary electrode AUX can be connected, preferably by way of a series resistor, either to a positive or a negative potential, or alternatingly to a positive and a negative potential of the operating voltage.

FIG. 6 shows an embodiment of the measurement circuit MC wherein the multi-polar switch S is connected on the one hand by way of the load resistor $R_{LOAD}$ to the auxiliary electrode AUX and can on the other hand be selectively switched between three positions, i.e. a measurement position MP, a first diagnostic position DP1, and a second diagnostic position DP2. In the measurement position MP the auxiliary electrode AUX is separated from the rest of the circuit. In the first diagnostic position DP1 the auxiliary electrode AUX is connected to a first potential of a second constant voltage source $U_{LOAD}$, and in the second diagnostic position DP2 the auxiliary electrode AUX is connected to the second potential of the second voltage source $U_{LOAD}$. The test voltage $U_{PT}$ can therefore be switched between two potentials.

In this circuit, a diagnostic current $I_{REF}$ is imposed on the auxiliary electrode AUX without the need to provide an additional voltage source. In order to give up the additional voltage source, a multi-polar switch S is used which can on the one hand be connected to a positive or a negative potential of the second voltage source and is, on the other hand, separated from the circuit while set to the measurement position MP. As the ISFET T is not needed during the diagnostic phase, the operating voltage $U_{CC}$ can be used advantageously to generate the test voltage $U_{PT}$, in other words to serve as voltage source $U_{LOAD}$.

Although the invention has been described through the presentation of specific exemplary embodiments, It is considered self-evident that numerous other variants are conceivable based on the teachings of the present invention, for example by combining features of the individual embodiments with each other and/or by exchanging individual functional units between the embodiments. In particular, all of the voltages described here, i.e. the supply voltage of the operational amplifier OA, the controlling voltage $U_{SET}$, the operating voltage $U_{CC}$, and the voltage source $U_{LOAD}$, can be derived from a single reference voltage source with the help of voltage dividers. It is also possible to use several voltage sources.

What is claimed is:

1. A measurement circuit, for use in a measurement probe that is measuring an ion concentration of a measurement medium and for diagnosing the operation of the measuring probe, which comprises a reference electrode, an auxiliary electrode and an ion-sensitive field effect transistor (ISFET) having a gate electrode that is coated with an ion-sensitive layer, such that the respective electrodes are immersible in the measurement medium, the measurement circuit comprising:
   a first voltage source, providing a constant voltage, with a first potential thereof that is connected to a drain terminal of the ISFET;
   a measurement resistor, with a first terminal thereof connected to a source terminal of the ISFET and a second terminal thereof connected to a second potential of the first voltage source;
   an operational amplifier, such that a non-inverting input thereof is connected to a settable controlling voltage, an inverting input thereof is connected to the first terminal of the measurement resistor, and an output thereof is connected to the reference electrode, and
   at least one controllable switch that can be switched between a measurement position, in which the measurement of the measurement medium takes place, and at least one diagnostic position, in which the diagnosis of the measuring probe takes place.

2. The measurement circuit of claim 1, wherein:
   in the diagnostic position, the auxiliary electrode is connected by way of a load resistor and the controllable switch to a constant test voltage, and
   in the measurement position, the auxiliary electrode is separated from the test voltage by means of the controllable switch.

3. The measurement circuit of claim 2, wherein the at least one controllable switch is a multi-polar switch, connected on the one hand to the first terminal of the measurement resistor and the inverting input of the operational amplifier and can, on the other hand, be set either to the measurement position which connects to the source terminal of the ISFET, or to the diagnostic position which connects to the auxiliary electrode, in which the auxiliary electrode is connected to the voltage that is present at the inverting input of the operational amplifier and corresponds at least approximately to the controlling voltage that is present at the non-inverting input of the operational amplifier.

4. The measurement circuit of claim 2, wherein the at least one controllable switch is a multi-polar switch, connected on the one hand to the first potential of the first voltage source and can, on the other hand, be set either to the measurement position which connects to the drain terminal of the ISFET, or to the diagnostic position, which connects by way of the load resistor to the auxiliary electrode.

5. The measurement circuit of claim 2, wherein:
   when the controllable switch is set to the diagnostic position, the auxiliary electrode is connected by way of the load resistor to a constant second voltage source which supplies a test voltage, and
   when the controllable switch is set to the measurement position, the auxiliary electrode can be separated from the second voltage source.

6. The measurement circuit of claim 2, wherein the controllable switch can be switched between a measurement position and at least a first diagnostic position and a second diagnostic position in which the auxiliary electrode is selectively connected, either directly or by way of the load resistor, to a potential of the first or second voltage source or to the superposition of potentials of the first and second voltage source.

7. The measurement circuit of claim 1, wherein the controllable switch is a controllable analog switch, preferably a CMOS transistor.

8. The measurement circuit of claim 1, wherein:
   when the controllable switch is set to the diagnostic position, the auxiliary electrode is connected by way of the load resistor to a constant second voltage source which supplies a test voltage, and
   when the controllable switch is set to the measurement position, the auxiliary electrode can be separated from the second voltage source.

9. The measurement circuit of claim 1, wherein the controllable switch can be switched between a measurement position and at least a first diagnostic position and a second diagnostic position in which the auxiliary electrode is selectively connected, either directly or by way of the load resistor, to a potential of the first or second voltage source or to the superposition of potentials of the first and second voltage source.

10. A probe for making a measurement of a measurement medium, the probe comprising:
    a housing;
    an ion-sensitive field effect transistor (ISFET), arranged in the housing, the ISFET comprising a gate electrode covered by an ion-sensitive layer;
    a reference electrode, arranged in the housing;
    an auxiliary electrode, arranged in the housing; and
    a measurement circuit according to claim 1;
    wherein the gate electrode, the reference electrode and the auxiliary electrode are each connected to the measurement circuit and arranged so that each reach into a measurement space to make contact with the measurement medium.

11. A method for measuring the ion concentration in a measurement medium with a measuring probe, and for diagnosing the operation of the measuring probe, wherein the measuring probe comprises a reference electrode designed for immersion in the measurement medium, an auxiliary electrode, also immersible in the measurement medium, and an ion-sensitive field effect transistor (ISFET), which has a coated gate electrode that makes contact with the measurement medium, a drain terminal is connected to a first potential of a constant first voltage source, and which also has a source terminal connected to a first terminal of a measurement resistor, a second terminal if which is connected to a second potential of the first voltage source, the probe also having an operational amplifier with a non-inverting input connected to a settable controlling voltage, an inverting input connected to the first terminal, and an output is connected to the reference electrode, and at least one controllable switch arranged to provide a measurement position, where a measurement mode is active in which the measurement of the measurement medium takes place, and at least one diagnostic position where a diagnostic mode is active in which the diagnosis of the operation of the measuring probe takes place, the method comprising the steps, in the diagnostic mode, of:
    applying a test voltage to the auxiliary electrode by way of a load resistor;
    measuring a first time profile of the voltage of at least one of: the reference electrode and the auxiliary electrode;

establishing at least one first comparison value by comparing a characteristic value or a characteristic curve to at least one of the measured first time profiles or to a difference between the first time profile of the voltage at the reference electrode and the first time profile of the voltage at the auxiliary electrode; and evaluating the established first comparison values to determine the condition of the reference electrode.

12. The method of claim 11, comprising, in the diagnostic mode, the further steps of:

after applying the test voltage and measuring the first time profile or profiles, separating the test voltage from the auxiliary electrode;

measuring a second time profile of at least one of: the reference electrode and the auxiliary electrode;

establishing at least one comparison value by comparing a characteristic value or a characteristic curve to at least one of the measured second time profiles or to a difference between the second time profile of the voltage at the reference electrode and the second time profile of the voltage at the auxiliary electrode; and evaluating the established second comparison values to determine the condition of the reference electrode.

13. The method of claim 11, wherein, when switching to the diagnostic mode, the controllable switch is used to separate the first voltage source from the source terminal or the drain terminal.

14. The method according to claim 11, wherein, when switching to the diagnostic mode, the controllable switch operates in one of the following manners:

the auxiliary electrode is connected by way of the load resistor, if applicable, to the first terminal and the inverting input of the operational amplifier, whereby the voltage at the inverting input, which corresponds to the controlling voltage, is used as the test voltage; or the auxiliary electrode is connected by way of the load resistor to a second voltage source, which supplies the test voltage; or the auxiliary electrode is connected by way of the load resistor to one of the potentials of the first voltage source, with the potential serving as the test voltage.

15. The method of claim 11, wherein the test voltage that is applied in the diagnostic mode to the auxiliary electrode by way of a load resistor is switched one or more times between two voltage values, preferably between a positive and a negative voltage value.

16. The method of claim 11, wherein the test voltage that is applied to the auxiliary electrode by way of a load resistor causes a first voltage pulse of a first polarity, a first predefined amplitude, and a first predefined duration.

17. The method of claim 11, wherein the test voltage that is applied to the auxiliary electrode by way of a load resistor is selected such that:

in a first diagnostic mode, a first voltage pulse of a first polarity, a first predefined amplitude, and a first predefined duration is applied to the auxiliary electrode; and in a second diagnostic mode, a second voltage pulse of a second polarity which is the opposite of the first polarity, a second predefined amplitude, and a second predefined duration is applied to the auxiliary electrode.

* * * * *